United States Patent [19]

Stautzenberger et al.

[11] 4,009,003
[45] Feb. 22, 1977

[54] METHOD FOR DETERMINING SUITABILITY OF TRIORGANOPHOSPHORUS LIGANDS FOR USE IN HYDROFORMYLATION PROCESSES

[75] Inventors: Adin Lee Stautzenberger; James Leonard Paul, both of Corpus Christi, Tex.

[73] Assignee: Celanese Corporation, New York, N.Y.

[22] Filed: Feb. 9, 1976

[21] Appl. No.: 656,546

[52] U.S. Cl. .................. 23/230 R; 252/431 R; 252/431 N; 252/431 P; 260/606.5 R
[51] Int. Cl.² .................. B01J 31/12; G01N 31/08
[58] Field of Search ............ 23/230 R; 252/431 R, 252/431 N, 431 P; 260/606.5 R

[56] References Cited
OTHER PUBLICATIONS

Chemical Abstracts I, 56:4791c, (1962).
Chemical Abstracts II, 80:107936p, (1974).

*Primary Examiner*—Morris O. Wolk
*Assistant Examiner*—Sidney Marantz

[57] ABSTRACT

The purity, and thus suitability of triorganophosphorus ligands of the same chemical composition obtained from different sources for use in forming catalytic complexes for catalyzing hydroformylation reactions is determined by heating an admixture of the organophosphorus ligand and an aldehyde, measuring the amount of resultant condensation products, and comparing said amount to a standard.

8 Claims, No Drawings

METHOD FOR DETERMINING SUITABILITY OF TRIORGANOPHOSPHORUS LIGANDS FOR USE IN HYDROFORMYLATION PROCESSES

BACKGROUND OF THE INVENTION

Processes for converting olefins to aldehydes and/or alcohols by the reaction of an olefin with carbon monoxide and hydrogen in the presence of a suitable catalytic complex in either batch or continuous processes are well known in the prior art, and are commonly referred to as oxo or hydroformylation processes.

Catalytic complexes commonly employed in the above processes are ex situ or in situ formed complexes of a transition metal, carbon monoxide, hydrogen and a suitable ligand, with excess ligand preferably being employed in the subsequent hydroformylation reaction. The metal employed is preferably a Group VIII metal, and even more preferably, is selected from rhodium, cobalt and iron. Rhodium is especially preferred since catalysts prepared therefrom permit the employment of commercially more desirable operating conditions. Suitable ligands will be described in greater detail hereinafter.

In the operation of the aforesaid process, it has been noted that the catalyst tends to exhibit relatively different initial activities and to undergo deactivation at relatively different rates depending upon the source of the ligands. These differences are believed to be attributable to impurities present in the ligand employed. More specifically, an impurity can bind directly with the Group VIII metal, e.g., rhodium, resulting in a reduced initial activity. Moreover, impurities can also catalyze aldehyde heavy end formation, resulting in the slow steady deactivation of the catalyst.

Since the catalyst life has a significant effect upon the commercial economics of the hydroformylation process due to the high catalyst cost and the necessity of purging the system to replace the catalyst, it is important to select the ligand permitting the formation of a catalyst which will be operable for the longest time period, i.e., the ligand having the greatest purity.

Prior to the present invention, no suitable method has been available for determining the relative purity of ligands of the same chemical structure obtained from different sources, thus providing a means whereby one might select an appropriate ligand for use in the formation of hydroformylation catalysts, or for other purposes.

SUMMARY OF THE INVENTION

It is a primary object of the present invention to provide a method for determining the purity of ligands having the same chemical composition, but obtained from different sources. In particular, it is an object of the present invention to provide a method for determining the purity, and thus suitability, of a given ligand in the preparation of catalytic complexes used in catalyzing hydroformylation reactions. Other objects, if not specifically set forth herein, will be obvious to the skilled artisan upon reading the detailed description of the invention which follows.

In essence, the method forming the present invention comprises preparing an admixture of an amount of the ligand to be tested with an amount of an aldehyde; heating said admixture for a given time period, e.g., by refluxing; determining the amount of reaction products formed; and comparing said amount of reaction products against a standard. In the selection of a suitable ligand, i.e., a given ligand of suitable purity, for use in the formation of a catalytic complex for use in a hydroformylation reaction, ligands are selected in which the ratio of reaction products obtained by refluxing the ligand and aldehyde to the standard is below a pre-determined value, said pre-determined value being based on economic considerations, such as ligand costs, catalyst costs and down-time losses.

DETAILED DESCRIPTION OF THE INVENTION

As used herein, the term "ligand" is intended to encompass triorgano compounds having the formula $MR_3$, wherein M is selected from the group consisting of phosphorus, antimony, tin, nitrogen and iron. R designates an aryl, alkyl or alkoxy radical having up to about 20 carbon atoms. It is to be understood that the R groups forming a given ligand need not all be of the same structure. Mixtures of ligands are also contemplated.

Because of their commercial significance, the present invention will be primarily described in terms of determining the purity, and selection, of ligands in which M is phosphorus, i.e., triorgano phosphorus ligands. Especially commercially significant ligands are the triarylphosphines, triarylphosphites, trialkylphosphites and tricycloalkyphosphites. Particularly significant are triphenylphosphine and triphenylphosphite.

The term "aldehyde" as used herein is intended to encompass the lower aldehydes, i.e., aldehydes having up to about 20 carbon atoms in their structure. Exemplary of such aldehydes are n-butyraldehyde, isobutyaldehyde, propionaldehyde, acetaldehyde, pentanal, hexanal, heptanal, 2-methyloctanal, and 3-methylhexanal. Preferably, the aldehyde selected in the same as the aldehyde product to be obtained in the subsequent hydroformylation reaction in which the liquid to be tested is employed. Mixtures of aldehydes are also contemplated.

In general the method of the present invention is comprised of the following steps:
 1. forming an admixture of a given ligand and a given aldehyde;
 2. forming a ligand-free test standard comprised of said given aldehyde;
 3. heating said admixture and said test standard under like conditions; and
 4. comparing the amount of reaction products from said admixture with the amount of reacting products from said test standard.

In the formation of the aforesaid admixture of ligand and aldehyde, generally from about 10 percent to about 40 percent, preferably about 20 to 30 percent, of ligand based upon the total admixture will be employed. If desired, a like amount of an inert material having a boiling point approximately that of the ligand being tested may be included in the test standard.

Heating may be conducted at any temperature sufficient to provide a reasonable amount of products within a reasonable time, and may be conducted under atmospheric or superatmospheric conditions. The duration of the heating will vary, of course, depending upon the particular ligand being tested and the aldehyde being used. Preferably, heating of the admixture is effected by refluxing.

In determining the suitability of a given ligand for use in forming a catalytic complex to be employed in a hydroformylation reaction the method of the present invention comprises the steps of:

1. Forming an admixture of said given ligand and an aldehyde, preferably the aldehyde product to be obtained in said hydroformylation reaction;
2. Forming a ligand-free test standard comprised of said aldehyde, preferably also containing an inert material having a boiling point approximately the boiling point of said ligand;
3. Heating said admixture of said test standard for a time sufficient to obtain a measurable amount of condensation products from said admixture; and
4. Determining whether the ratio between the condensation products in said admixture and in said test standard is less than a predetermined number.

As aforementioned, said pre-determined number is selected taking into consideration such factors as ligand costs, catalyst costs, and operational losses due to down time of the reactor.

The following examples will serve to illustrate the present invention, but are not to be taken as in limitation thereof.

EXAMPLE I

An admixture was formed of samples of 20% triphenylphosphine from various sources and 80% n-butyraldehyde. The admixture was refluxed for 164 hours. The following table compares the results obtained in comparison with the blank consisting of n-butyraldehyde.

Table I

| % | Blank | Sample A | Sample B | Sample C | Sample D |
|---|---|---|---|---|---|
| 2-Ethylhexenal | 0.08 | 1.1 | 0.55 | 0.28 | 0.10 |
| HOBu | 1.0 | 0.7 | 1.35 | 1.0 | 0.7 |
| Ester[a] | 1.01 | 5.5 | 2.99 | 2.04 | 0.96 |
| Unknowns | 0.5 | 0.3 | 0.3 | 0.3 | 0.3 |
| Total | 2.59 | 7.6 | 5.19 | 3.62 | 2.06 |

Ester[a] is believed to be a mixture of the two Tischenko ester isomers derived from n-BuH and n-butyraldol.

EXAMPLE II

The above analysis was also run using heptanal as the aldehyde instead of n-butyraldehyde. Comparable results were obtained. It was only necessary to reflux the admixture, however, for about two hours.

It will be understood that many modifications and variations of the foregoing description may be made without departing from the spirit and scope of the invention. For example, one may analyze a particular component, e.g., 2-ethylhexenal, and base the aforesaid pre-determined number on the value obtained instead of the total amount of condensation products.

We claim:

1. A method for determining the purity of a triorganophosphorus ligand comprising the steps of:
   a. forming an admixture of said ligand and an aldehyde;
   b. forming a ligand-free test standard comprised of said aldehyde;
   c. heating said admixture and said test standard under like conditions; and
   d. comparing the amount of reaction products from said admixture with the amount of reaction products from said test standard.

2. The method of claim 1, wherein said ligand comprises from about 10 to about 40 percent of said admixture.

3. The method of claim 2, wherein said ligand-free test standard is further comprised of an inert material having a boiling point approximating that of said ligand.

4. The method of claim 1, wherein said ligand is triphenylphosphine.

5. The method of claim 1, wherein said aldehyde is n-butyraldehyde.

6. A method for determining the suitability of a triorganophosphorus ligand for use in forming a catalytic complex to be employed in a hydroformylation reaction comprising the steps of:
   a. forming an admixture of said ligand and an aldehyde;
   b. forming a ligand-free test standard comprised of said aldehyde;
   c. heating said admixture and said test standard for a time sufficient to obtain a measurable amount of condensation products from said admixture; and
   d. determining whether the ratio between the condensation products in said admixture and in said test standard is less than a predetermined number.

7. The method of claim 6, wherein said ligand is triphenylphosphine.

8. The method of claim 6, wherein said aldehyde is n-butyraldehyde.

* * * * *